(12) United States Patent
Williams et al.

(10) Patent No.: US 6,528,503 B2
(45) Date of Patent: Mar. 4, 2003

(54) THROMBIN INHIBITORS

(75) Inventors: Peter D. Williams, Harleysville, PA (US); Terry A. Lyle, Lederach, PA (US); Matthew M. Morrissette, Pottstown, PA (US); Lekhanh O. Tran, Norristown, PA (US); Donnette D. Staas, Harleysville, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/171,708

(22) Filed: Jun. 14, 2002

(65) Prior Publication Data

US 2003/0013700 A1 Jan. 16, 2003

Related U.S. Application Data

(63) Continuation-in-part of application No. 10/023,776, filed on Dec. 18, 2001.
(60) Provisional application No. 60/323,184, filed on Sep. 18, 2001, and provisional application No. 60/256,304, filed on Dec. 18, 2000.

(51) Int. Cl.[7] ...................... A61K 31/397; C07D 205/04
(52) U.S. Cl. .................... 514/210; 548/953; 546/268.1; 514/340
(58) Field of Search ................................ 514/210, 340; 548/953; 546/268.1

(56) References Cited

U.S. PATENT DOCUMENTS

| | | |
|---|---|---|
| 2,277,409 A | 3/1942 | Murray |
| 4,346,078 A | 8/1982 | Bajusz et al. |
| 4,703,036 A | 10/1987 | Bajusz et al. |
| 4,804,743 A | 2/1989 | Kaltenbronn et al. |
| 5,252,566 A | 10/1993 | Shuman |
| 5,332,726 A | 7/1994 | Klein et al. |
| 5,380,713 A | 1/1995 | Balasubramanian et al. |
| 5,416,093 A | 5/1995 | Shuman |
| 5,510,369 A | 4/1996 | Lumma et al. |
| 5,792,779 A | 8/1998 | Sanderson et al. |
| 5,798,377 A | 8/1998 | Lumma et al. |
| 5,866,573 A | 2/1999 | Sanderson et al. |
| 5,869,487 A | 2/1999 | Coburn et al. |
| 6,004,976 A | 12/1999 | Coburn |
| 6,011,038 A | 1/2000 | Dorsey et al. |
| 6,017,934 A | 1/2000 | Sanderson et al. |
| 6,051,568 A * | 4/2000 | Gustafsson et al. ......... 514/210 |
| 6,087,373 A | 7/2000 | Coburn et al. |
| 6,147,078 A | 11/2000 | Sanderson et al. |
| 6,239,132 B1 | 5/2001 | Coburn et al. |

FOREIGN PATENT DOCUMENTS

| | | |
|---|---|---|
| EP | 0 185 210 | 6/1986 |
| EP | 0 195 212 A2 | 9/1986 |
| EP | 0 363 284 A2 | 4/1990 |
| EP | 0 471 651 A2 | 2/1992 |
| EP | 0 479 489 A2 | 4/1992 |
| EP | 0 601 459 A2 | 6/1994 |
| EP | 603112 A1 | 6/1994 |
| EP | 0 648 780 A1 | 4/1995 |
| EP | 0 672 658 A1 | 9/1995 |
| WO | WO 92/07869 | 5/1992 |
| WO | WO 92/14750 | 9/1992 |
| WO | WO 94/29336 | 12/1994 |
| WO | WO 96/31504 | 10/1996 |
| WO | Wo 96/32110 | 10/1996 |
| WO | WO 00/75134 A1 | 12/2000 |
| WO | WO 01/38323 | 5/2001 |
| WO | WO 02/09711 A1 | 2/2002 |
| WO | WO 02/50056 A1 | 6/2002 |
| WO | WO 02/064559 A2 | 8/2002 |

OTHER PUBLICATIONS

Henriksen, D. B. et al., *Int. J. Peptide Protein Res.*, "Peptide amidation by enzymatic transacylation and photolysis" Vo. 41, pp. 169–180 (1993).
Bajusz, S. et al., *J. Med. Chem.*, "Highly Active and Selective Anticoagulants: D–Phe–Pro–Arg–H, a Free Tripeptide Aldehyde Prone to Spontaneous Inactivation, and Its Stable N–Methyl Derivative, D–MePhe–Pro–Arg–H" vol. 33, pp. 1729–1735 (1990).
Berndt, M. C. et al., *Gordon(ed) Platelets in Biology and Pathology–2*, "Platelet membrane proteins: composition and receptor function", pp. 43–75 (1981).
Martin, B. M. et al., *Biochemistry*, "Platelet Stimulation by Thrombin and Other Proteases", Vo. 14, No. 6, pp. 1308–1314 (1975).
Greco, N.J. et al., *Blood*, "PPACK–Thrombin Inhibits Thrombin–Induced Platelet Aggregation and Cytoplasmic Acidification but Does Not Inhibit Platelet Shape Change", vol. 75, No. 10 (May 15), pp. 1983–1990 (1990).
Bode, W. et al, *The EMBO Journal*, "The refined 1.9 A crystal structure of human a–thrombin: interaction with D–Phe–Pro–Arg chloromethylketone and significance of the Tyr–Pro–Pro–Trp insertion segment", vol. 8, No. 11, pp. 34 67–3475 (1989).

(List continued on next page.)

*Primary Examiner*—Charanjit S. Aulakh
(74) *Attorney, Agent, or Firm*—Richard S. Parr; Valerie J. Camara

(57) ABSTRACT

Compounds of the invention are useful in inhibiting thrombin and associated thrombotic occlusions having the following structure:

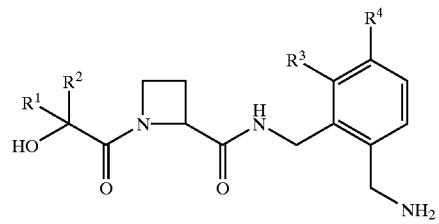

or a pharmaceutically acceptable salt thereof, e.g. 1-(3(S)-Cyclopropyl-2(R)-hydroxybutanoyl)azetidine-2(S)-N-(2-aminomethyl-5-chlorobenzyl)carboxamide, and 1-(3-Cyclopropyl-3-methyl-2(R)-hydroxybutanoyl)azetidine-2(S)-N-(2-aminomethyl-5-chlorobenzyl)carboxamide.

11 Claims, No Drawings

OTHER PUBLICATIONS

Workman, E. F. et al., *The Journal of Biological Chemistry*, "Structure–Function Relationships in the Interaction of a–Thrombin with Blood Platelets",, vol. 252, No. 20, pp. 7118–7123 (1992).

Hui, K. Y. et al, *Biochemical and Biophysical Research Communications*, "Minimal Sequence Requirement of Thrombin Receptor Agonist Pepride", vol. 184, No. 2, pp. 790–796 (1992).

Scarborough, R. M. et al., *The Journal of Biological Chemistry*, "Tethered Ligand Agonist Peptides—Structural Requirements for Thrombin Receptor Activation Reveal Mechanism of Proteolytic Unmasking of Agonist Function", vol. 267, No. 19, pp. 13146–13149 (1992).

Vassallo Jr, R.R. et al., *The Journal of Biological Chemistry*, "Structure–Function Relationships in the Activation of Platelet Thrombin Receptors by Receptor–derived Peptides", Vo. 267, No. 9, pp. 6081–6085 (1992).

Iwanowicz, E.J. et al., *Organic and Medicinal Chemistry Letters*, "a–Hydroxy–and a–Ketoester Functionalized Thrombin Inhibitors", vol. 2, No. 12, pp. 1607–1612 (1992).

Okumura, T. et al, *The Journal of Biological Chemistry*, "Platelet Glycocalicin—Interaction with Thrombin and Role as Thrombin Receptor of the Platelet Surface", vol. 263. No. 10, pp. 3435–3443 (1978).

Tollefsen, D. M. et al., *The Journal of Biological Chemistry*, "The BInding of Thrombin to the Surface of Human Platelets", vol. 249, No. 8, pp. 2646–2651 (1974).

Vu et al., *Cell*, "Molecular Cloning of a functional Thrombin Receptor Reveals a Novel Proteolytic Mechanism of Receptor Activation", vol. 64, pp. 1057–1068 (1991).

Gronke, R.S. et al., *The Journal of Biological Chemistry*, "Thrombin Interaction with Platelets—Influence of a Platelet Protease Nexin", vol. 262, No. 7, pp. 3030–3036 (1987).

Phillips, *Thrombos. Diathes. haemorrh. (Stuttg.)*, "Thrombin interaction with Human PLatelets Potentiation of Thrombin–induced Aggregation and Release by Imactivated Thrombin", vol. 32, pp. 207–215 (1974).

Balasubramanian, N. et al., *J. Med. Chem.*, "Active Site–Directed Synthetic Thrombin Inhibitors: Synthesis, in Vitro and in Vivo Activity Profile of BMY 44621 and Analogs. An Examination of the Role of the Amino Group in the D–Phe–Pro–Arg–H Series", vol. 36, pp. 300–303 (1993).

Kettner, C. et al., *The Journal of Biological Chemistry*, "The Selective Inhibition of Thrombin by Peptides of Boroarginine", vol. 265, No. 30, pp. 18289–18297 (1990).

Shuman, R. T. et al., *Journal of Medicinal Chem.*, "Highly Selective Tripeptide Thrombin Inhibitors", vol. 36, No. 3, pp. 314–319 (1993).

Hussain, M. A. et al., *Peptides*, "Anticoagulant Activity of a Peptide Boronic Acid Thrombin Inhibitor by Various Routes of Administration in Rats", vol. 12, pp. 1153–1154 (1991).

Vencill, C. F. et al., *Chemical Abstracts*, vol. 103, Abstract No. 18900 (1986).

Edwards, P. D. et al., *J. Am. Chem. Soc.*, "Design, Synthesis, and Kinetic Evaluation of a Unique Class of Elastase Inhibitors, the Peptidyl a–Ketobenzoxazoles, and the X–ray Crystal Structure of the Covalent Complex between Porcine Pancreatic Elastae and Ac–Ala–Pro–Val–2–Benzoxazole", vol. 114, pp. 1854–1863 (1992).

Banner, D. et al., *Perspect. Med. Chem.*, "Serine Proteases: 3DStructures, Mechanisms of Action and Inhibitors", Chapter 3, pp. 29–43 (1993).

Tapparelli, C. et al., *TIPS*, "Synthric low–molecular weight thrombin inhibitors: molecular design and pharmacological profile" vol. 14, pp. 366–376 (1993).

* cited by examiner

THROMBIN INHIBITORS

CROSS-REFERENCE TO APPLICATIONS

This application is a continuation-in-part application of U.S. Ser. No. 10/023,776, filed Dec. 18, 2001, which is related to provisional applications U.S. Ser. Nos. 60/323,184, filed Sep. 18, 2001, and 60/256,304, filed Dec. 18, 2000.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., J. Amer. Chem. Soc., (1992) vol. 114, pp. 1854–63, describes peptidyl α-ketobenzoxazoles, which are reversible inhibitors of the serine proteases human leukocyte elastase and porcine pancreatic elastase. European Publication 363 284 describes analogs of peptidase substrates in which the nitrogen atom of the scissile amide group of the substrate peptide has been replaced by hydrogen or a substituted carbonyl moiety. Australian Publication 86245677 also describes peptidase inhibitors having an activated electrophilic ketone moiety such as fluoromethylene ketone or α-keto carboxyl derivatives. R. J. Brown et al., J. Med. Chem., Vol. 37, pages 1259–1261 (1994) describes orally active, non-peptidic inhibitors of human leukocyte elastase which contain trifluoromethylketone and pyridinone moieties. H. Mack et al., J. Enzyme Inhibition, Vol. 9, pages 73–86 (1995) describes rigid amidino-phenylalanine thrombin inhibitors which contain a pyridinone moiety as a central core structure. U.S. Pat. Nos. 5,536,708, 5,672,582, 5,510,369 and 5,741,485 describe proline-based thrombin inhibitors having cyclohexylamino end groups. The present invention includes thrombin inhibitors having phenyl ring end groups substituted with aminomethyl moieties, which have been found to provide therapeutically effective thrombin inhibitors having desirable potency and pharmacokinetic properties.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION

Compounds of the invention are useful as thrombin inhibitors and have therapeutic value in for example, preventing coronary artery disease.

This invention includes compounds of the general formula

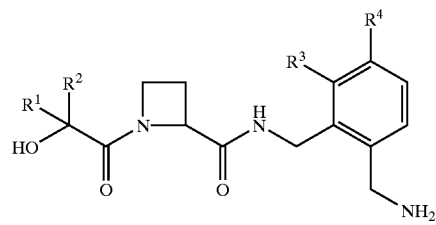

or a pharmaceutically acceptable salt thereof, wherein
$R^1$ and $R^2$ are independently selected from the group consisting of
1) hydrogen,
2) $C_{1-6}$ alkyl,
3) $C_{1-6}$ alkyl substituted with one, two or three members, same or different, selected from the group consisting of
  i) hydroxyl,
  ii) halogen,
  iii) $C_3$,
  iv) phenyl,
  v) phenyl, substituted with one, two or three members, same or different, selected from the group consisting of
    a) hydroxyl,
    b) halogen,
    c) $CF_3$,
    d) $C_{1-6}$ alkyl,
    e) $C_{1-4}$ alkoxyl,
    f) amino,
    g) $C_{1-4}$ alkylamino, and
    h) $CH_3C(O)NH$—,
  vi) pyridyl,
  vii) pyridyl substituted with one or two members, same or different, selected from the group consisting of
    a) halogen,
    b) $C_{1-4}$ alkoxyl, and
    c) $C_{1-6}$ alkyl,
  viii) pyridyl N-oxide
  ix) pyridyl N-oxide substituted with one or two members, same or different, selected from the group consisting of
    a) halogen,
    b) $C_{1-4}$ alkoxyl, and
    c) $C_{1-6}$ alkyl,
  x) $C_{3-6}$ cycloalkyl, and
  xi) $C_{3-6}$ cycloalkyl substituted with $C_{1-4}$ alkyl or halogen,
4) $C\equiv C-R^8$,
5) phenyl,
6) phenyl substituted with one, two or three members, same or different, selected from the group consisting of
  i) hydroxyl,
  ii) halogen,
  iii) $CF_3$,
  iv) $C_{1-6}$ alkyl, v) C$_{1-4}$ alkoxyl,
vi) amino,
vii) C$_{1-4}$ alkylamino, and
viii) CH$_3$C(O)NH—,
7) pyridyl,
8) pyridyl substituted with one or two members, same or different, selected from the group consisting of
i) halogen,
ii) C$_{1-4}$ alkoxyl, and
iii) C$_{1-6}$ alkyl,
9) pyridyl N-oxide,
10) pyridyl N-oxide substituted with one or two members, same or different, selected from the group consisting of
i) halogen,
ii) C$_{1-4}$ alkoxyl, and
iii) C$_{1-6}$ alkyl,
11) C$_{3-6}$ cycloalkyl, and
12) C$_{3-6}$ cycloalkyl substituted with C$_{1-4}$ alkyl or halogen;

R$^3$ is hydrogen or halogen;

R$^4$ is halogen;

R$^8$ is selected from the group consisting of
1) hydrogen,
2) C$_{1-6}$ alkyl,
3) C$_{3-6}$ cycloalkyl, and
4) C$_{3-6}$ cycloalkyl substituted with C$_{1-4}$ alkyl or halogen, provided that when R$^3$ is hydrogen, R$^4$ is Cl.

In a class of compounds or pharmaceutically acceptable salts thereof of the invention, R$^3$ is hydrogen or F, and R$^4$ is Cl or F, provided that when R$^3$ is hydrogen, R$^4$ is Cl.

In a subclass of the class of compounds or pharmaceutically acceptable salts thereof, R$^2$ is hydrogen or C$_{1-6}$ alkyl.

In a group of this subclass or pharmaceutically acceptable salts thereof, R$^1$ is 1) C$_{1-6}$ alkyl, unsubstituted or substituted with one, two, or three members, same or different, selected from the group consisting of
i) cyclopropyl, and
ii) cyclopropyl substituted with C$_{1-4}$ alkyl,
C≡CC(CH$_3$)$_3$, or
phenyl substituted with Cl.

Examples of this group of compounds are listed below:

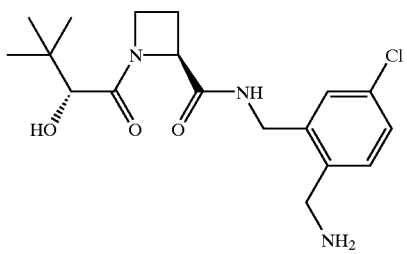

1(3,3-Dimethyl-2(R)-hydroxybutanoyl)azetidine-2(S)-N-(2-aminomethyl-5-chlorobenzyl)carboxamide (1)

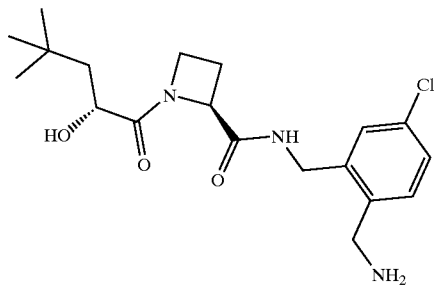

1-(4,4-Dimethyl-2(R)-hydroxypentanoyl)azetidine-2(S)-N-(2-aminomethyl-5-chlorobenzyl)carboxamide (2)

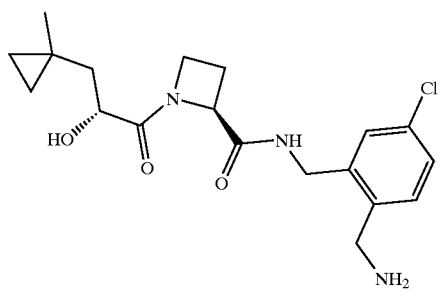

1-(3-(1-Methylcyclopropyl)-2(R)-hydroxypropanoyl)azetidine-2(S)-N-(2-aminomethyl-5-chlorobenzyl)carboxamide (3)

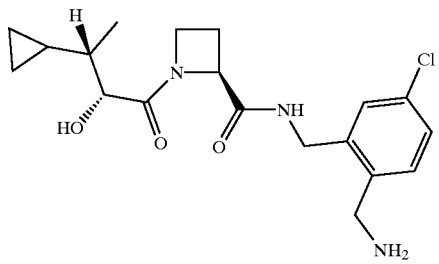

1-(3(S)-Cyclopropyl-2(R)-hydroxybutanoyl)azetidine-2(S)-N-(2-aminomethyl-5-chlorobenzyl)carboxamide (4)

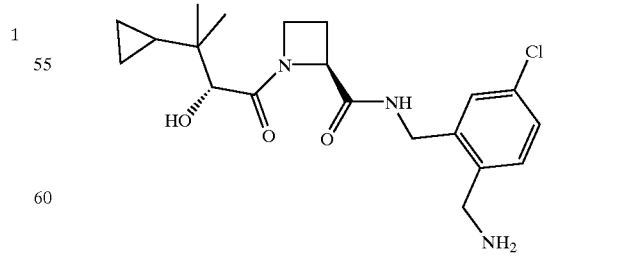

1-(3-Cyclopropyl-3-methyl-2(R)-hydroxybutanoyl)azetidine-2(S)-N-(2-aminomethyl-5-chlorobenzyl)carboxamide (5)

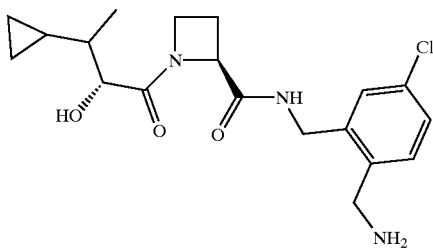

1-(3(R)-Cyclopropyl-2(R)-hydroxybutanoyl)azetidine-2(S)-N-(2-aminomethyl-5-chlorobenzyl)carboxamide (4)

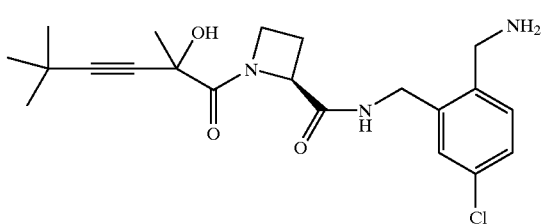

1-(2-hydroxy-2,5,5-trimethyl-3-hexynoyl)azetidine-2(S)-N-(2-aminomethyl-5-chlorobenzyl)carboxamide (7)

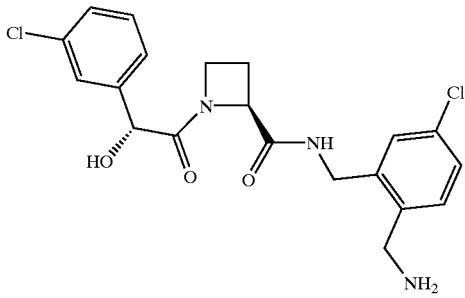

1-(2(R)-hydroxy(3-chlorophenyl)acetyl)azetidine-2(S)-N-(2-aminomethyl-5-chlorobenzyl)carboxamide (8)

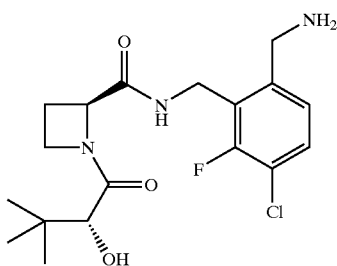

1-(3-Cyclopropyl-3-methyl-2(R)-hydroxybutanoyl)azetidine-2(S)-N-(2-aminomethyl-6-fluoro-5-chlorobenzyl)carboxamide (9)

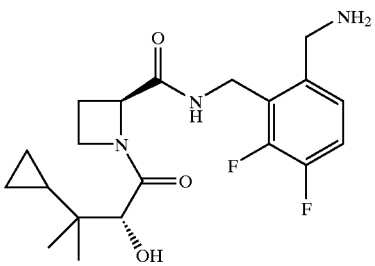

1-(3,3-Dimethyl-2(R)-hydroxybutanoyl)azetidine-2(S)-N-(2-aminomethyl-5,6-difluorobenzyl)carboxamide (10)

The compounds of the present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being, included in the present invention.

When any variable occurs more than one time in any constituent or in formula I, its definition on each occurrence is independent of its definition at every other occurrence. Also, combinations of substituents and/or variables are permissible only if such combinations result in stable compounds.

Some abbreviations that may appear in this application are as follows:

| Designation | |
|---|---|
| Boc | tert-butyloxycarbonyl |
| DBU | 1,8-diazabicyclo[5.4.0]undec-7-ene |
| DMF | dimethylformamide |
| DPPA | diphenylphosphoryl azide |
| EDC | 1-ethyl-3-(3-dimethylaminopropyl)carbodiimide hydrochloride |
| EtOAc | ethyl acetate |
| Fmoc | 9-fluorenylmethoxycarbonyl |
| HCl | hydrochloric acid |
| HOBT | 1-hydroxybenzotriazole |
| HPLC | high pressure liquid chromatography |
| LiAlH$_4$ | lithium aluminum hydride |
| LCMS | liquid chromatography mass spectrum |
| LDA | lithium diisopropylamide |
| MeOH | methanol |
| MgSO$_4$ | magnesium sulfate |
| NaOH | sodium hydroxide |
| Pd(PPh$_3$)$_4$ | tetrakis triphenylphosphine palladium |
| PPh$_3$ | triphenylphosphine |
| THF | tetrahydrofuran |
| TLC | thin layer chromatography |
| Zn(CN)$_2$ | zinc cyanide |

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxyl" represents a linear or branched alkyl group of indicated number of carbon atoms attached through an oxygen bridge; "halogen", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "$C_{3-6}$ cycloalkyl" is intended to include cyclopropyl, cyclobutyl, cyclopentyl, cyclohexyl and cycloheptyl, and the like.

The term "aryl" as used herein except where noted, represents a stable 6- to 10-membered mono- or bicyclic ring system such as phenyl, or naphthyl. The aryl ring can be unsubstituted or substituted with one or more of $C_{1-4}$ lower alkyl; hydroxy; alkoxy; halogen; amino.

The pyridyl N-oxide portion of the compounds of the invention are structurally depicted using conventional representations

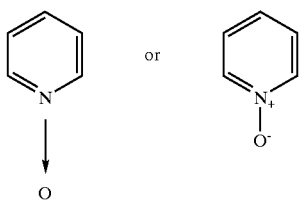

which have equivalent meanings.

In this specification methyl substituents may be represented by

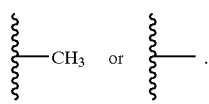

For example, the structures

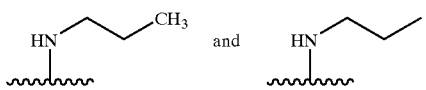

have equivalent meanings.

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0. 1–2.5 mg/kg/day, and most preferably 0.1–0.5 mg/kg/day (unless specified otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

Unless other wise stated, all NMR determinations were made using 400 MHz field strength.

SCHEME 1

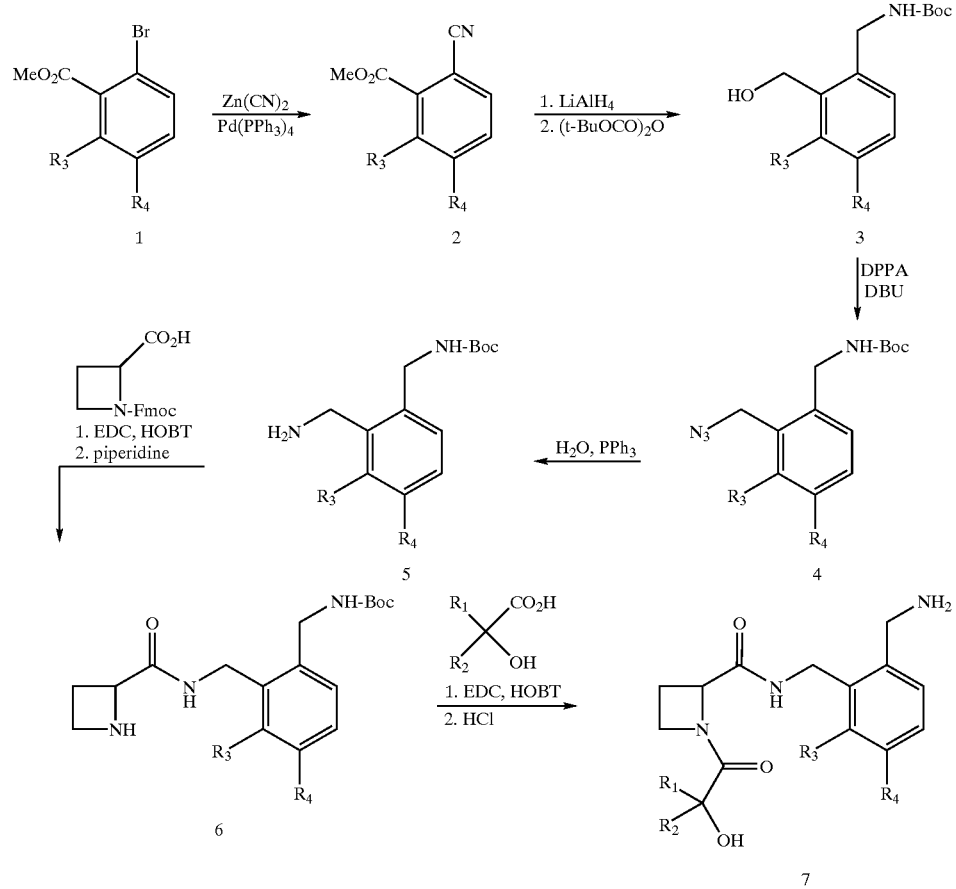

SCHEME 2

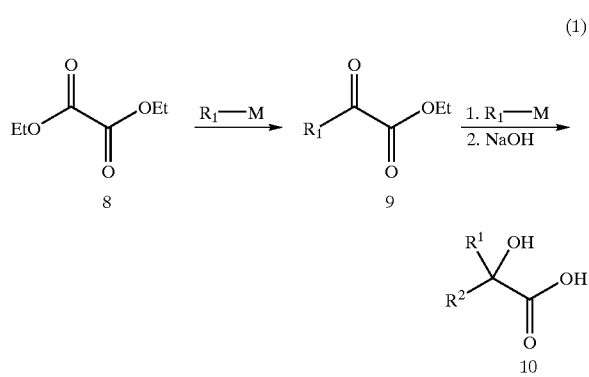

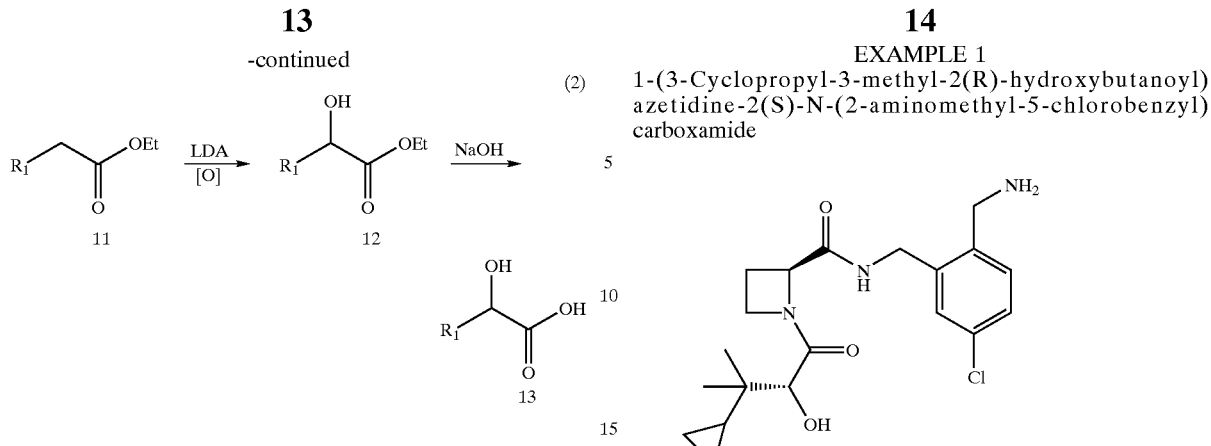

Compounds of the present invention are synthesized using procedures and chemical intermediates which are well known to those of ordinary skill in the art. The compounds of the present invention are essentially comprised of three subunits, referred to as the P1, P2 and P3 subunits, which are connected together by two amide bonds. The central subunit, the P2 subunit, is an amino acid. This P2 amino acid is connected at its carboxy end via an amide bond to the P1 subunit, a benzylamine derivative, and this P2 amino acid is connected at its amino end via an amide bond to the P3 subunit which is a hydroxy acid. Standard amino acid coupling procedures and protecting group chemistry enables synthesis of the final compounds in either direction, i.e., the P2-P1 amide bond may be formed first, followed by formation of the P3-P2 amide bond, or the P3-P2 amide bond may be formed first, followed by formation of the P2-P1 amide bond. Standard protecting group chemistry may be employed, if necessary, in the P1 and P3 subunits to allow selective amide bond formation between the various subunits. After the subunits have been connected via the two amide bonds to give a P3-P2-P1 structure, any additional protecting groups that may present in the P1 and or P3 subunits can be removed using standard procedures to give final compounds. Scheme 1 shows a synthesis in which the P1 and P2 amide bond is formed first, and the P3 amide bond is formed last. These P1 subunits are comprised of a halogen-substituted, mono-protected bis-benzylamine derivative. A synthesis of such a bis-benzylamine derivative is shown in Scheme 1. Bromo ester 1 is cyanated to give an ortho-cyano ester, 2. Both the ester and cyano groups are then reduced to give an amino alcohol which is protected on nitrogen to give intermediate 3. The alcohol in 3 is then converted to an azide, 4, and the azido group is reduced to give the mono-protected bis-benzylamine derivative 5. The amino group in 5 is then acylated with N-protected azetitdine-2-carboxylic acid and the azetitine protecting group is removed to give 6. The azetidine nitrogen in 6 is then acylated with a hydroxy ester, and the remaining benzylamine protecting group is removed to give final compound 7. The hydroxy acid used in this sequence can be made in several ways. Scheme 2 shows two methods. The first method involves addition of an organometallic (R1-M) to an oxalate ester to give alpha keto ester 9. Addition of a second organometallic (R2-M) or hydride reagent to keto ester 9, followed by ester hydrolysis, gives hydroxy acid 10. Another way of making hydroxy acids for use in Scheme 1 involves deprotonation of ester 11, and oxidation of the resulting ester enolate with a reagent such as an oxaziridine to give hydroxy ester 12. Saponification of the ester in 12 gives hydroxy acid 13.

EXAMPLE 1

1-(3-Cyclopropyl-3-methyl-2(R)-hydroxybutanoyl) azetidine-2(S)-N-(2-aminomethyl-5-chlorobenzyl) carboxamide Step 1. methyl 2-bromo-5-chlorobenzoate Into a stirred solution of 2-bromo-5-chlorobenzoic acid (11 g, 46.7 mmol, HPLC RT=2.99 min) in methanol (250 mL) at 0° C. was bubbled HCl gas. The reaction was allowed to warm to room temperature and stirred overnight. The reaction mixture was concentrated in vacuo to give an orange oil, which was purified by flash chromatography using hexanes as eluant to give methyl 2-bromo-5-chlorobenzoate as a colorless oil (10.7 g, 92% yield). TLC $R_f$=0.6 (5% EtOAc-hexanes); HPLC RT=3.48 min (Method A); $^1$H NMR (CDCl$_3$, 400 MHz) 7.78 ppm (d, 1H, J=2.6 Hz); 7.59 ppm (d, 1H, J=12.81 Hz);7.30 ppm (dd, 1H, J=8.6, 2.5 Hz); 3.94 ppm (s, 3H).

Step 2. methyl 5-chloro-2-cyanobenzoate

To a stirred solution of methyl 2-bromo-5-chlorobenzoate (11.5 g, 46 mmol) in degassed DMF (50 mL) was added zinc cyanide (2.82 g, 24.0 mmol) and palladium tetrakis-triphenylphosphine (1.0 g, 0.86 mmol) and the mixture was heated to 90° C. for 18 h. The reaction was partitioned between EtOAc (200 mL) and water (100 mL). The organic phase was concentrated in vacuo and the residue was purified by flash chromatography eluting with a gradient of 10%, 15%, 20% ethyl acetate in hexane yielding methyl 5-chloro-2-cyanobenzoate as a white solid (8.0 g, 88% yield). TLC $R_f$=0.4 (15% EtOAc-hexanes); HPLC RT=3.13 min (Method A); $^1$H NMR (CDCl$_3$, 400 MHz) 8.13 ppm (d, 1H, J=1.83 Hz); 8.09 ppm (d, 1H, J=8.24 Hz); 7.29 ppm (dd, 1H, J=8.34, 2.10 Hz); 4.02 ppm (s, 3H).

Step.3 2-aminomethyl-5-chlorobenzyl alcohol

To a stirred solution of lithium aluminum hydride (104 mL of a 1.0 molar solution in ether, 104 mmol) in anhydrous THF (200 mL) at 0° C. was added methyl 5-chloro-2-cyanobenzoate (9.28 g, 47 mmol) in anhydrous THF (15 mL). After 1 h, the reaction was quenched at 0° C. with water (3.9 mL), 3.0 N aqueous NaOH (4.0 mL, 12 mmol) and water (3.9 mL). Ether (200 mL) was added and the thick precipitate which had formed was removed by filtration and washed with THF. The filtrate was concentrated in vacuo and the crude product, 2-aminomethyl-5-chlorobenzyl alcohol, was used immediately in the next step. $^1$H NMR (CDCl$_3$, 400 MHz) 7.17–7.36 ppm (m, 3H); 4.60 ppm (s, 2H); 3.98 ppm (s, 2H).

Step 4. 2-(tert-butyloxycarbonylaminomethyl)-5-chlorobenzyl alcohol

To a solution of crude 1-hydroxymethyl-2-aminomethyl-5-chlorobenzene from the previous step in dichloromethane (200 mL) was added di-tert-butyl dicarbonate (11.38 g, 52.18 mmol) at room temperature. After one hour, the reaction was partitioned with water (200 mL). The organic layer was concentrated in vacuo and the residue was purified by flash chromatography eluting a gradient of 20%, 30%, 40% EtOAc in hexane. The brown oil which resulted was taken up in dichloromethane (500 mL) and treated with activated charcoal to give 2-(tert-butyloxycarbonylaminomethyl)-5-chlorobenzyl alcohol as an off-white solid (9.2 g, 72% yield over two steps). TLC $R_f$=0.3 (25% EtOAc-hexanes); HPLC RT=3.15 min (Method A); LC-MS m/z=272; $^1$H NMR (CDCl$_3$, 400 MHz) 7.36 ppm (s, 1H); 7.2–7.5 ppm (m, 2H); 4.69 ppm (b s, 2H); 4.32 ppm (d, 2H, J=6.04 Hz); 1.43 ppm (s, 9H).

Step 5. 1-azidomethyl-2-(tert-butyloxycarbonylaminomethyl)-5-chlorobenzene

To a stirred solution of 2-(tert-butyloxycarbonyl-aminomethyl)-5-chlorobenzyl alcohol (10 g, 36.8 mmol) in anhydrous THF (100 mL) at 0° C. was added DPPA (8.3 mL, 38.6 mmol) and DBU (5.79 mL, 38.6 mmol). The mixture was stirred for 1 h at 0° C. and then for 18 h at ambient temperature. The mixture was partitioned between EtOAc (250 mL) and water (100 mL). The organic layer was washed with brine and was concentrated in vacuo. The residue was purified by flash chromatography, eluting with a gradient of 10%, 15%, 20% EtOAc in hexane to give 1-azidomethyl-2-(tert-butyloxycarbonylaminomethyl)-5-chlorobenzene as an oil (9.2 g, 85% yield). HPLC RT=3.65 min (Method A); LC-MS m/z=152 (parent ion not observed); $^1$H NMR (CDCl$_3$, 400 MHz) 7.25–7.39 ppm (m, 3H); 4.41 ppm (s, 2H), 4.32 ppm (d, 2H, J=5.86 Hz); 1.45 ppm (s, 9H).

Step 6. 2-(tert-butyloxycarbonylaminomethyl)-5-chlorobenzylamine

To a stirred solution of 1-azidomethyl-2-(tert-butyloxycarbonylaminomethyl)-5-chlorobenzene (10.9 g, 36.73 mmol) in THF (60 mL) and water (6 mL) was added triphenylphospine (10.59 g, 40.40 mmol). The reaction was heated to 50° C. and stirred for 18 h. The reaction was concentrated in vacuo and the residue was purified by flash chromatography using a gradient elution of 2%, 3%, 4%, 5% A in dichloromethane (A=95:5 MeOH:NH$_4$OH). Concentration of product-containing fractions in vacuo gave 2-(tert-butyloxycarbonylaminomethyl)-5-chlorobenzylamine as a solid (8.8 g, 88% yield). TLC $R_f$=0.3 (95:5:0.25 CH$_2$Cl$_2$:MeOH:NH$_4$OH); HPLC RT=2.64 min (Method A); LC-MS m/z=271; $^1$H NMR (CDCl$_3$, 400 MHz) 7.21–7.52 ppm (m, 3H); 4.32 ppm (b d, 2H); 3.90 ppm (s, 2H); 1.44 ppm (s, 9H).

Step 7. 1-(fluorenylmethoxycarbonyl)azetidine-2(S)-N-(2-tert-butyloxycarbonylaminomethyl-5-chlorobenzyl)carboxamide To 1-(fluorenylmethoxycarbonyl)azetidine-2(S)-carboxylic acid (2.43g, 7.53 mmol) in 20 mL of DMF at ambient temperature under nitrogen atmosphere was added 2-(tert-butyloxycarbonylaminomethyl)-5-chlorobenzylamine (2.038 g, 7.53 mmol), HOBT hydrate (1.12 g, 8.28 mmol), EDC (2.16 g, 11.29 mmol), and the pH of the mixture was brought to pH=6 (as measured on wetted E. Merck pH strips) by the slow addition of diisopropyl-ethylamine (approx. 0.8 mL). The mixture was stirred at ambient temperature for 3 hours and was concentrated in vacuo. The residue was partitioned between EtOAc and saturated sodium bicarbonate solution. The organic layer was dried (Na$_2$SO$_4$), filtered, and concentrated in vacuo. The residue was purified by flash silica gel chromatography using 100% CH$_2$Cl$_2$ then 1% MeOH in CH$_2$Cl$_2$ as an eluent. Desired fractions were concentrated in vacuo to afford 1-(fluorenylmethoxycarbonyl)azetidine-2(S)N-(2-tert-butyloxycarbonylaminomethyl-5-chlorobenzyl)carboxamide as a white foam (2.95 g; HPLC RT=3.82 min, Method A; LC-MS m/z=576.21; 400 MHz $^1$H NMR, CDCl$_3$, 8.7 ppm (bs, 1H), 7.74 ppm (d, J=7.32 Hz, 2H), 7.57 ppm (d, J=7.32 Hz, 2H), 7.38 ppm (t, J=7.33 Hz, 2H), 7.24–7.32 ppm (m, 2H), 4.77 ppm (t, J=7.61 Hz, 1H), 4.3–4.45ppm (m, 2H), 4.15–4.3 ppm (m, 1H), 3.95–4.15 ppm (m, 2H), 2.3–2.6 ppm (m, 2H)).

Step 8. azetidine-2(S)-N-(2-tert-butyloxycarbonylaminomethyl-5-chlorobenzyl)carboxamide To a stirred solution of piperidine (39.18 mL, 395.73 mmol) in 30 mL of THF at ambient temperature was added solution of 1-(fluorenylmethoxycarbonyl)azetidine-2(S)-N-(2-tert-butyloxycarbonylaminomethyl-5-chlorobenzyl)carboxamide (7.6 g, 13:19 mmol) from the previous step dissolved in 30 mL of THF dropwise over 1 h. The mixture was stirred at ambient temperature for 4 hours and was concentrated in vacuo. The residue was purified by flash silica gel chromatography using 1%, 2%, 5%, then 10% MeOH in CH$_2$Cl$_2$ as an eluent. Desired fractions were concentrated in vacuo to afford azetidine-2(S)-N-(2-tert-butyloxycarbonylaminomethyl-5-chlorobenzyl)carboxamide as a white foam (4.01 g; HPLC RT=2.69 min, Method A; LC-MS m/z=354.24).

Step 9. methyl 3-cyclopropyl-3-methylbutanoate

To a solution of diethyl zinc (77 mL of a 1.0 M solution in hexane; 77 mmol) in dry dichloromethane (250 mL) at 0° C. under an inert atmosphere was added TFA (5.9 mL, 77 mmol) in dichloromethane (15 mL) dropwise over a period of 1 h. To this suspension was added diiodomethane (6.2 mL, 77 mmol) in dichloromethane (10 mL) dropwise over a period of 15 min. The resulting solution was stirred at 0° C. for 30 min, at which time methyl 3,3-dimethyl-4-pentenoate (5.0 g, 35 mmol) was added. The mixture was stirred at 0° C. for 30 min and then at ambient temperature for 16 h. The reaction was quenched by addition of saturated aqueous ammonium chloride (100 mL). The organic layer was separated and washed with water (100 mL), dried (MgSO$_4$), filtered, and the solvents were removed under reduced pressure. The resulting liquid was distilled under reduced pressure. The fraction boiling at 76–80° C. (18 mm Hg) was collected to give methyl 3-cyclopropyl-3-methylbutanoate as a colorless liquid. $^1$H NMR 400 MHz, CDCl$_3$, 3.66 ppm (s, 3H), 2.27 ppm (s, 2H), 0.87 ppm (s, 6H), 0.81 ppm (m, 1H), 0.31 ppm (m, 2H), 0.20 ppm (m, 2H)

Step 10. methyl 2-hydroxy-3-cyclopropyl-3-methylbutanoate

To a stirred solution of diisopropylamine (4.9 mL, 35 mmol) in dry THF (100 mL) at 0° C. under inert atmosphere was added n-butyllithium (14 mL, 35 mmol) dropwise over a period of 5 min. The solution was cooled to –78 ° C. and methyl 3-cyclopropyl-3-methylbutanoate (5.0 g, 32) was added dropwise over a period of 5 min. The solution was stirred at –78 ° C. for 1 h at which time (+)-camphorsulfonyloxaziridine (9.0 g, 39 mmol) was added all at once. The resulting suspension was stirred at –78 ° C. for 30 min and then allowed to warm to ambient temperature over 30 min. EtOAc (100 mL) and saturated aqueous ammonium chloride (50 mL) were added and the organic layer was separated and washed with water (50 mL), dried (MgSO$_4$), and filtered. The solvents were removed under reduced pressure and the resulting oily solid was stirred in ether (50 mL) for 30 min. The solid was removed by filtration and the filtrate solvent was removed under reduced pressure. The residue was purified by flash column chromatography using a gradient elution of 10% to 14% EtOAc in hexanes to give methyl 2-hydroxy-3-cyclopropyl-3-methylbutanoate as a colorless liquid. TLC $R_f$=0.4 (12%

EtOAc-hexanes); HPLC RT=2.72 min (Method A); $^1$H NMR 400 MHz, CDCl$_3$, 3.92 ppm ((d, J=7.9 Hz, 1H), 3.79 ppm (s, 3H), 2.79 ppm (d, J=7.9 Hz, 1H), 0.84 ppm (s, 3H), 0.83 ppm (m, 1H), 0.80 ppm (s, 3H), 0.32 ppm (m, 2H), 0.20 ppm (m, 2H)

Step 11. 2(R)-hydroxy-3-cyclopropyl-3-methylbutanonoic acid

To a stirred solution of give methyl 2-hydroxy-3-cyclopropyl-3-methylbutanoate (4.6 g, 27 mmol) in MeOH (30 mL) was added aqueous NaOH (7.0 mL of a 5.0 M solution, 35 mmol). The mixture was stirred at ambient temperature for 18 h. The mixture was brought to pH 2 by the addition of 6 N aqueous HCl, and the solvents were removed under reduced pressure. The residue was dried under high vacuum for 18 hours. The residue was suspended in dichloromethane (50 mL) and the mixture was stirred for 1 h. The solid was removed by filtration and the filtrate solvent was removed under reduced pressure to give an oil. This material was purified using a Chiralpak AD column using 93.5:7.5:0.1 hexanes:EtOH:TFA as the eluant. The major, first eluting peak was collected and after removal of the solvents under reduced pressure and drying under high vacuum for 18 h, 2(R)-hydroxy-3-cyclopropyl-3-methylbutanonoic acid was obtained a white solid. HPLC RT=2.28 min (Method A); $^1$H NMR 400 MHz, CDCl$_3$, 4.01 ppm (s, 1H), 0.91 ppm (s, 3H), 0.88 ppm (m, 1H), 0.85 ppm (s, 3H), 0.36 ppm (m, 2H), 0.27 ppm (m, 2H)

Step 12. 1-(3-Cyclopropyl-3-methyl-2(R)-hydroxybutanoyl)azetidine-2(S)-N-(2-tert-butyloxycarbonylaminomethyl-5-chlorobenzyl)carboxamide To a stirred solution azetidine-2(S)-N-(2-aminomethyl-5-chlorobenzyl)carboxamide (2.0 g, 5.65 mmol, HPLC RT=2.66 min), 2(R)-hydroxy-3-cyclopropyl-3-methylbutanonoic acid (~0.89 g, 5.65 mmol), and HOBT hydrate (0.86 g, 5.65 mmol) in DMF (20 mL) was added EDC (1.42 g, 7.4 mmol). Diisopropylethylamine was then added slowly in portions (0.8 mL total) to bring the pH of the solution to 6–7 as measured on wetted E. Merck pH indicator strips. The mixture was stirred at ambient temperature for 1 h, at which time HPLC analysis indicated complete consumption of the azetidine starting material. Water (5 mL) was added and the solvents were removed under reduced pressure. The residue was partitioned between EtOAc (100 mL) and saturated aqueous NaHCO$_3$ (50 mL). The EtOAc layer was separated, dried over anhydrous MgSO$_4$, and filtered. The filtrate solvent was removed under reduced pressure and the residue was purified by flash chromatography using a gradient elution of 1:1 to 2:1 A:hexanes (A=2:98 MeOH:EtOAc). 1-(3-Cyclopropyl-3-methyl-2(R)-hydroxybutanoyl)azetidine-2(S)-N-(2-tert-butyloxycarbonylaminomethyl-5-chlorobenzyl)carboxamide was obtained as a colorless gum (2.5 g; TLC R$_f$=0.7 (EtOAc); HPLC RT=3.35 min, method A; LC-MS m/z=494).

Step 13. 1-(3-Cyclopropyl-3-methyl-2(R)-hydroxybutanoyl)azetidine-2(Si-N-(2-aminomethyl-5-chlorobenzyl)carboxamide 1-(3-Cyclopropyl-3-methyl-2(R)-hydroxybutanoyl)azetidine-2(S)-N-(2-tert-butyloxycarbonylaminomethyl-5-chlorobenzyl)carboxamide from the previous step (2.5 g, 5.1 mmol) was dissolved in ether (20 mL) and cooled with stirring to 0° C. A solution of anhydrous HCl in ether (25 mL of a 1 Molar solution, 25 mmol) was added slowly. The resulting solution was stirred at 0 °C. for 10 min, and then at ambient temperature for 20 h. The solvent was removed under reduced pressure and the residue was purified by preparative reverse-phase HPLC using an acetonitrile:water gradient containing 0.1% TFA. The product-containing fractions were combined and lyophilized to give the trifluoroacetate salt of the title compound as a white solid (HPLC RT=2.50 min, Method A; LC-MS m/z=394).

EXAMPLE 2

1-(3,3-Dimethyl-2(R)-hydroxybutanoyl)azetidine-2(S)-N-(2-aminomethyl-5-chlorobenzyl)carboxamide

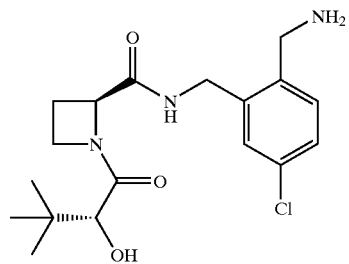

Step 1. 2(R)-Hydroxy-3.3-dimethylbutanoic acid

To a stirred solution of 2(R)-amino-3,3-dimethylbutyric acid (5.0 g, 38.1 mmol) in 80 mL of 1 N sulfuric acid at –10° C. was slowly added a solution of sodium nitrite (5.26 g, 76.2 mmol) dissolved in 25 mL of water. After the addition was complete, the reaction was gradually warmed to ambient temperature and stirred for 20 h. Sodium chloride (10 g) was added and the solution was extracted twice with 100 mL portions of ether. The combined organic layers were dried over anhydrous sodium sulfate and filtered. The filtrate solvent was removed under reduced pressure. The residue was purified by preparative HPLC using a Chiralpak AD column (5 cm×50 cm) using 5% ethanol in 95% hexanes with 0.2% TFA as the mobile phase at a flow rate of 80 mL/min. The product-containing fractions were concentrated in vacuo. 2(R)-Hydroxy-3,3-dimethylbutanoic acid was obtained as an oil that crystallized on standing (2.2 g; 44%); $^1$H NMR, 400 MHz, CDCl$_3$, 6.0–7.0 ppm (v br s, 2H), 3.91 ppm (s, 1H), 1.03 ppm (s, 9H).

Step 2. 1-(3,3-dimethyl-2(R)-hydroxybutanoyl)azetidine-2(S)-N-(2-tert-butyloxycarbonylaminomethyl-5-chlorobenzyl)carboxamide 2(R)-Hydroxy-3,3-dimethylbutanoic acid from Step 1 above was coupled to azetidine-2(S)-N-(2-aminomethyl-5-chlorobenzyl)carboxamide from Step 8 of Example 1 using the procedure given in Step 12 of Example 1 to give 1-(3,3-dimethyl-2(R)-hydroxybutanoyl)azetidine-2(S)-N-(2tert-butyloxycarbonylaminomethyl-5-chlorobenzyl)carboxamide.

Step 3. 1-(3.3-Dimethyl-2(R)-hydroxybutanoyl)azetidine-2(S)-N-(2-aminomethyl-5-chlorobenzyl)carboxamide HCl gas was bubbled into a stirred solution of 1-(3,3-dimethyl-2(R)-hydroxybutanoyl)azetidine-2(S)-N-(2-tert-butyloxycarbonylaminomethyl-5-chlorobenzyl)carboxamide in EtOAc at 0° C. for 10 minutes. The mixture was stirred at 0° C. for 1 h and then the solvent was removed under reduced pressure. The residue was purified by preparative reverse-phase chromatography using an acetonitrile:water gradient containing 0.1% TFA. Product-containing fractions were combined and lyophilized to give the TFA salt of the title compound as an amorphous solid (HPLC RT=2.36 min, Method A; LC-MS m/z=368.29; 400 MHz $^1$H NMR, CD$_3$OD, 7.48 ppm (d, 1H), 7.4 ppm (d, 2H), 4.71 ppm (m, 1H), 4.61 ppm (d, 1H), 4.36 ppm (m, 2H), 4.3 ppm (d, 1H), 4.25ppm (q, 2H), 2.7 ppm (m, 1H), 2.23 ppm (m, 1H), 0.98 ppm (s, 9H)).

EXAMPLE 3
1-(3-(1-Methylcyclopropyl)-2(R)-hydroxypropanoyl)azetidine-2(S)-N-(2-aminomethyl-5-chlorobenzyl)carboxamide

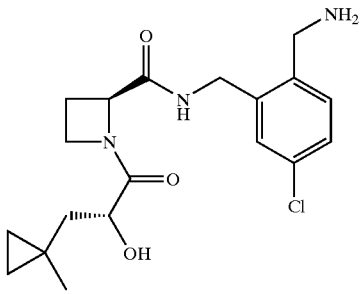

Step 1. ethyl 3-(1-methyl-cyclopropyl)propanoate

To a solution of diethyl zinc (31 mL of a 1.0 M solution in hexane, 31 mmol) in dry dichloromethane (100 mL) at 0° C. under an inert atmosphere was added TFA (2.4 mL, 31 mmol) in dichloromethane (5 mL) dropwise over a period of 30 min. To this suspension was added diiodomethane (2.5 mL, 31 mmol) in dichloromethane (5 mL) dropwise over a period of 10 min. The resulting solution was stirred at 0° C. for 30 min, at which time ethyl 4-methyl-4-pentenoate (2.0 g, 14 mmol) was added. The mixture was stirred at 0° C. for 30 min and then at ambient temperature for 18 h. The reaction was quenched by addition of saturated aqueous ammonium chloride (50 mL). The organic layer was separated and washed with water (50 mL), dried (MgSO$_4$), filtered, and the solvents were removed under reduced pressure. The residue was purified by flash column chromatography using 5% EtOAc-hexanes as eluant to give ethyl 3-(1-methyl-cyclopropyl)propanoate as a colorless liquid. TLC R$_f$=0.5 (5% EtOAc-hexanes); HPLC RT=3.43 min (Method A); $^1$H NMR 400 MHz, CDCl$_3$, 4.12 ppm (q, J=8 Hz, 2H), 2.38 ppm (t, J=8 Hz, 2H), 1.57 ppm (t, J=8 Hz, 2H), 1.26 ppm, (t, J=8 Hz, 3H), 1.02 ppm (s, 3H), 0.28 ppm (m, 2H), 0.25 ppm (m, 2H)

Step 2. ethyl 2-hydroxy-3-(1-methyl-cyclopropyl)propanoate

To a stirred solution of diisopropylamine (1.9 mL, 13 mmol) in dry THF (20 mL) at 0° C. under inert atmosphere was added n-butyllithium (5.2 mL of a 2.5 M solution in hexane, 13 mmol) dropwise over a period of 5 min. The solution was cooled to −78° C. and ethyl 3-(1-methyl-cyclopropyl)propanoate (1.87 g, 12 mmol) was added dropwise over a period of 5 min. The solution was stirred at −78° C. for 1 h at which time (+)-camphorsulfonyloxaziridine (3.5 g, 15 mmol) was added all at once. The resulting suspension was stirred at −78° C. for 30 min and then allowed to warm to ambient temperature over 30 min. EtOAc (50 mL) and saturated aqueous ammonium chloride (25 mL) were added and the organic layer was separated and washed with water (20 mL), dried (MgSO$_4$), and filtered. The solvents were removed under reduced pressure and the resulting oily solid was stirred in ether (15 mL) for 30 min. The solid was removed by filtration and the filtrate solvent was removed under reduced pressure. The residue was purified by flash column chromatography using a gradient elution of 10% to 15% EtOAc in hexanes to give ethyl 2-hydroxy-3-(1-methyl-cyclopropyl)propanoate as a colorless liquid. TLC R$_f$=0.5 (20% EtOAc-hexanes); HPLC RT=2.73 min (Method A); $^1$H NMR 400 MHz, CDCl$_3$, 4.31 ppm (M, 1H)4.23 ppm (m, 2H), 2.65 ppm (d, J=6.1 Hz, 1H), 1.76 ppm (dd, J=4.2, 14.6 Hz, 1H), 1.54 ppm (dd, J=8.4, 14.6 Hz, 1H), 1.30 (t, J=8 Hz, 3H), 1.14 ppm (s, 3H), 0.42 ppm (m. 1H), 0.30 ppm (m, 3H)

Step 3. 2(R)-hydroxy-3-(1-methyl-cyclopropyl)propanoic acid

To a stirred solution of methyl 2-hydroxy-3-(1-methyl-cyclopropyl)propanoate (1.4 g, 8.1 mmol) in EtOH (10 mL) was added aqueous NaOH (2.2 mL of a 5.0 M solution, 11 mmol). The mixture was stirred at ambient temperature for 18 h. The mixture was brought to pH 2 by the addition of 6 N aqueous HCl and the solvents were removed under reduced pressure. The residue was dried under high vacuum for 18 hours. The residue was suspended in dichloromethane (15 mL) and the mixture was stirred for 1 h. The solid was removed by filtration and the filtrate solvent was removed under reduced pressure to give an oil. This material was purified using a Chiralpak AD column using 95:5:0.1 hexanes:2-propanol:TFA as the eluant. The first eluting peak was collected and after removal of the solvents under reduced pressure and drying under high vacuum for 18 h, 2(R)-hydroxy-3-(1-methyl-cyclopropyl)propanoic acid was obtained a white solid. HPLC RT=2.00 min (Method A)

Step 4. 1-(3-(1-methylcyclopropyl)-2(R)-hydroxypropanoyl)azetidine-2(S)-N-(2-tert-butyloxycarbonylaminomethyl-5-chlorobenzyl)carboxamide 2(R)-Hydroxy-3-(1-methyl-cyclopropyl)propanoic acid from Step 3 above was coupled to azetidine-2(S)-N-(2-aminomethyl-5-chlorobenzyl)carboxamide from Step 8 of Example 1 using the procedure given in Step 12 of Example 1 to give 1-(3-(1-methylcyclopropyl)-2(R)-hydroxypropanoyl)azetidine-2(S)-N-(2-tert-butyloxycarbonylaminomethyl-5-chlorobenzyl)carboxamide.

Step 5. 1-(3-(1-Methylcyclopropyl)-2(R)-hydroxypropanoyl)azetidine-2(S)-N-(2-aminomethyl-5-chlorobenzyl)carboxamide 1-(3-(1-Methylcyclopropyl)-2(R)-propanoyl)azetidine-2(S)-N-(2-tert-butyloxycarbonylaminomethyl-5-chlorobenzyl)carboxamide was deprotected and purified using the procedure given in Step 3 of Example 2 to give the TFA salt of the title compound as an amorphous solid (HPLC RT=2.39 min, Method A; LC-MS m/z=380.33; 400 MHz $^1$H NMR, CD$_3$OD, 7.48 ppm (d, 1H), 7.4 ppm (d, 2H), 4.56 ppm (d, 1H), 4.42 ppm (d, 1H), 4.2–4.4 ppm (m, 5H), 2.7 ppm (m, 1H), 2.45 ppm (m, 1H), 1.7 ppm (m, 1H), 1.2 ppm (s, 3H), 0.2–0.5 ppm (m, 4H)).

EXAMPLE 4
1-(3(S)-Cyclopropyl-2(R)-hydroxybutanoyl)azetidine-2(S)-N(2-aminomethyl-5-chlorobenzyl)carboxamide

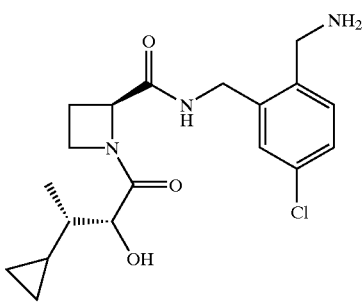

Step 1. methyl 2-benzyloxy-3-cyclopropylbutanoate

To a stirred solution of syn-2-benzyloxy-3-methyl-4-pentenoic acid (prepared by the method of Kallmerten, et al., J. Org. Chem., Vol. 52, 1987, p. 3889; 1.1 g, 5.0 mmol) at 0° C. in ether (25 mL) was added a solution of diazomethane in ether (approximately 20 mmol in 100 mL of ether). The mixture was stirred at 0° C. for 10 min, then at ambient temperature for 1 h. The solution was cooled to 0° C. and Pd(OAc)$_2$ (approximately 25 mg) was added. The mixture was stirred at 0° C. for 30 min and then at ambient temperature for 16 h. The ether was removed under reduced pressure and the residue was purified by flash column chromatography, using a gradient elution of 10% to 15% EtOAc-hexanes as eluant, to give methyl 2-benzyloxy-3-cyclopropylbutanoate as an oil. TLC R$_f$=0.5 (15% EtOAc-hexanes); HPLC RT=3.1 min (Method A); LC-MS m/z=249; $^1$H NMR 400 MHz, CDCl$_3$, 7.3–7.4 ppm (m, 5H), 4.74 ppm (d, J=12 Hz, 1H), 4.42 ppm (d, J=12 Hz, 1H), 3.91 ppm (d, J=4.5 Hz, 1H), 3.75 ppm (s, 3H), 1.07 ppm (overlapping s and m, 4H), 0.75 ppm (m, 1H), 0.48 ppm (m, 1H), 0.34 ppm (m, 1H), 0.08 ppm (m, 2H)

Step 2. methyl 2-hydroxy-3-cyclopropylbutanoate

To a stirred solution of methyl 2-benzyloxy-3-cyclopropylbutanoate (1.0 g, 4.0 mmol) and acetic acid (1 mL) in MeOH (25 mL) was added 10% palladium on charcoal (100 mg). Hydrogen gas was bubbled though the stirred solution for several minutes, and the reaction mixture was stirred under an atmosphere of hydrogen for 6 h. Nitrogen gas was bubbled through the solution to purge all of the hydrogen and the catalyst was removed by filtration. The filtrate solvents were removed under reduced pressure and the residue was partitioned between dichloromethane and saturated aqueous sodium bicarbonate. The organic layer was separated, dried (MgSO$_4$), filtered, and the solvent was removed under reduced pressure to give methyl 2-hydroxy-3-cyclopropylbutanoate as a colorless oil. HPLC RT=2.47 min (Method A); LC-MS m/z=159; $^1$H NMR 400 MHz, CDCl$_3$, 4.25 ppm (dd, J=3.3, 6.5 Hz, 1H), 3.77 ppm (s, 3H), 2.72 ppm (d, J=6.6 Hz, 1H), 1.05 ppm (m, 1h) 0.95 ppm (d, J=7 Hz, 3H), 0.84 ppm (m, 1H), 0.50 ppm (m, 2H), 0.19 ppm (m, 1H), 0.10 ppm (m, 1H)

Step 3. 2(R)-hydroxy-3(S)-cyclopropylbutanoic acid

To a stirred solution of methyl 2-hydroxy-3-cyclopropylbutanoate (0.62 g, 3.9 mmol) in MeOH (10 mL) was added aqueous NaOH (1.0 mL of a 5.5 M solution, 5.5 mmol). The mixture was stirred at ambient temperature for 18 h. The mixture was brought to pH 2 by the addition of 6 N aqueous HCl and solvents were removed under reduced pressure. The residue was dried under high vacuum for several hours. The residue was suspended in dichloromethane (15 mL) and stirred for 1 h. The solid was removed by filtration and the filtrate solvent was removed under reduced pressure. The residue was purified on a Chiralpak AD column using 90:10:0.1 hexanes:2-propanol:TFA as eluant. Fractions containing the first-eluting peak were pooled and the solvents were removed under reduced pressure to give 2(R)-hydroxy-3(S)-cyclopropylbutanoic acid as a white solid. HPLC RT=1.98 min (Method A); $^1$H NMR 400 MHz, CDCl$_3$, 4.36 ppm (d, J=2.9 Hz, 1H), 1.18 ppm (m, 1H), 1.00 ppm (d, J=7 Hz, 3H), 0.86 ppm (m, 1H), 0.54 ppm (m, 2H), 0.23 ppm (m, 1H), 0.18 ppm (m, 1H)

Step 4. 1-(3(S)-cyclopropyl-2(R)-hydroxylbutanoyl) azetidine-2(S)-N-(2-tert-butyloxycarbonylaminomethyl-5-chlorobenzyl)carboxamide 2(R)-Hydroxy-3(S)-cyclopropylbutanoic acid from Step 3 above was coupled to azetidine-2(S)-N-(2-aminomethyl-5-chlorobenzyl)carboxamide from Step 8 of Example 1 using the procedure given in Step 12 of Example 1 to give 1-(3(S)-cyclopropyl-2(R)-hydroxylbutanoyl)azetidine-2(S)-N-(2-tert-butyloxycarbonylaminomethyl-5-chlorobenzyl) carboxamide.

Step 5. 1-(3(S)-Cyclopropyl-2(R)-hydroxybutanoyl) azetidine-2(S)-N-(2-aminomethyl-5-chlorobenzyl) carboxamide 1-(3(S)-Cyclopropyl-2(R)-hydroxylbutanoyl)azetidine-(S)-N-(2-tert-butyloxycarbonylaminomethyl-5-chlorobenzyl)carboxamide was deprotected and purified using the procedure given in Step 3 of Example 2 to give the TFA salt of the title compound as an amorphous solid (HPLC RT=2.38 min, Method A; LC-MS m/z=380.26).

EXAMPLE 5

1-(4,4-Dimethyl-2(R)-hydroxypentanoyl)azetidine-2(S)-N-(2-aminomethyl-5-chlorobenzyl)carboxamide

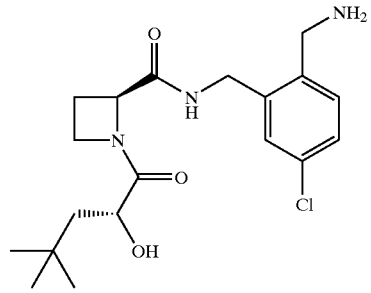

Step 1. 4,4-dimethyl-2(R)-hydroxypentanoic acid 4,4-Dimethyl-2(R)-aminopentanoic acid was converted to 4,4-dimethyl-2(R)-hydroxypentanoic acid using the procedure given in Step 1 of Example 2.

Step 2. 1-(4,4-dimethyl-2(R)-hydroxypentanoyl)azetidine-2(S)-N-(2-tert-butyloxycarbonylaminomethyl-5-chlorobenzyl)carboxamide 4,4-Dimethyl-2(R)-hydroxypentanoic acid was coupled to azetidine-2(S)-N-(2-aminomethyl-5-chlorobenzyl) carboxamide from Step 8 of Example 1 using the procedure given in Step 12 of Example 1 to give 1-(4,4-dimethyl-2 (R)-hydroxypentanoyl)azetidine-2(S)-N-(2-tert-butyloxycarbonylaminomethyl-5-chlorobenzyl) carboxamide.

Step 3. 1-(4,4-Dimethyl-2(R)-hydroxypentanoyl)azetidine-2(S)-N-(2-aminomethyl-5-chlorobenzyl)carboxamide 1-(4,4-Dimethyl-2(R)-hydroxypentanoyl)azetidine-2(S)-N-(2-tert-butyloxycarbonylaminomethyl-5-chlorobenzyl) carboxamide was deprotected and purified using the procedure given in Step 3 of Example 2 to give the TFA salt of the title compound as an amorphous solid (HPLC RT=2.55 min, Method A; LC-MS m/z=382.26; 400 MHz $^1$H NMR, CD$_3$OD, 7.48 ppm (d, 1H), 7.4 ppm (d, 2H), 4.71 ppm (m, 1H), 4.56 ppm (d, 1H), 4.42 ppm (d, 1H), 4.2–4.36 ppm (m, 4H), 2.56 ppm (m, 1H), 2.26 ppm (m, 1H), 1.46–1.58 ppm (m, 2H), 0.98 ppm (s, 9H)).

EXAMPLE 6

1-(2(R)-hydroxy(3-chlorophenyl)acetyl)azetidine-2(S)-N-(2-aminomethyl-5-chlorobenzyl)carboxamide

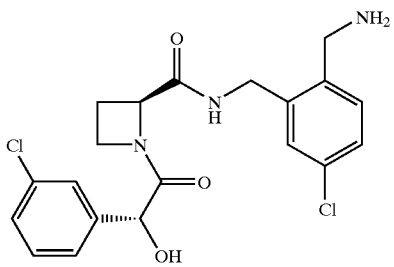

Step 1. 1-(2(R)-hydroxyl(3-chlorophenyl)acetyl)azetidine-2(S)-N-(2-tert-butyloxycarbonylaminomethyl-5-chlorobenzyl)carboxamide 2(R)-Hydroxy(3-chlorophenyl)acetic acid was coupled to azetidine-2(S)-N-(2-aminomethyl-5-chlorobenzyl)carboxamide from Step 8 of Example 1 using the procedure given in Step 12 of Example 1 to give -(2(R)-hydroxyl(3-chlorophenyl)acetyl)azetidine-2(S)-N-(2-tert-butyloxycarbonylaminomethyl-5-chlorobenzyl)carboxamide.

Step 2. 1-(2(R)-hydroxy(3-chlorophenyl)acetyl)azetidine-2(S)-N-(2-aminomethyl-5-chlorobenzyl)carboxamide 1-(2(R)-Hydroxyl(3-chlorophenyl)acetyl)azetidine-2(S)-N-(2-tert-butyloxycarbonylaminomethyl-5-chlorobenzyl)carboxamide was deprotected and purified using the procedure given in Step 3 of Example 2 to give the TFA salt of the title compound as an amorphous solid (HPLC RT=2.55 min, Method A; LC-MS m/z=422.18). HPLC Method A:

| Stationary Phase: | Hewlett-Packard Zorbax SB-C8 column 75 × 4.6 mm, 3.5 micron |
|---|---|
| Mobile Phase: | A = H$_2$O containing 0.1% by volume TFA B = CH$_3$CN containing 0.1% by volume TFA Gradient: 95:5 A:B to 0:100 A:B over 4.5 minutes Flow Rate: 3.0 mL/min |

UV Detection at 215 nm

Typical tablet cores suitable for administration of thrombin inhibitors are comprised of, but not limited to, the following amounts of standard ingredients:

| Excipient | General Range (%) | Preferred Range (%) | Most Preferred Range (%) |
|---|---|---|---|
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

In Vitro Assay For Determining Proteinase Inhibition

Assays of human α-thrombin and human trypsin were performed by the methods substantially as described in Thrombosis Research, Issue No. 70, page 173 (1993) by S. D. Lewis et al.

The assays were carried out at 25° C. in 0.05 M TRIS buffer pH 7.4, 0.15 M NaCl, 0.1% PEG. Trypsin assays also contained 1 mM CaCl$_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human α-thrombin ($K_m$=125 μM) and bovine trypsin ($K_m$=125 μM).

p-Nitroanilide substrate concentration was determined from measurements of absorbance at 342 nm using an extinction coefficient of 8270 cm$^{-1}$M$^{-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate benzyloxycarbonyl-Gly-Pro-Arg-7-amino-4-trifluoromethylcoumarin (Z-GPR-afc, Lewis S. D. et al. (1998) J. Biol. Chem. 273, pp. 4843–4854) ($K_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≦0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in the following equation.

$$V_o/V_i = 1 + [I]/K_i$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

EXAMPLE 7

Tablet Preparation

Tablets containing 25.0, 50.0, and 100.0 mg., respectively, of the following active compounds are prepared as illustrated below (compositions A–C). Active I is compound 1-(3-Cyclopropyl-3-methyl-2(R)-hydroxybutanoyl)azetidine-2(S)-N-(2-aminomethyl-5-chlorobenzyl)carboxamide.

| | Amount-(mg) | | |
|---|---|---|---|
| Component | A | B | C |
| Active I | 25 | 50 | 100 |
| Microcrystalline cellulose | 37.25 | 100 | 200 |
| Modified food corn starch | 37.25 | 4.25 | 8.5 |
| Magnesium stearate | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 8

Tablet Preparation

Exemplary compositions of compound 1-(3-Cyclopropyl-3-methyl-2(R)-hydroxybutanoyl)azetidine-2(S)-N-(2-aminomethyl-5-chlorobenzyl)carboxamide (Active I) tablets are shown below:

| Component | 0.25 mg | 2 mg | 10 mg | 50 mg |
|---|---|---|---|---|
| Active I | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet preparation via direct compression

Active I, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet preparation via dry granulation

Alternatively, a dry powder blend is compacted under modest forces and remilled to afford granules of specified particle size. The granules are then mixed with magnesium stearate and tabletted as stated above.

EXAMPLE 9

Intravenous Formulations

Intravenous formulations of compound 1-(3-Cyclopropyl-3-methyl-2(R)-hydroxybutanoyl)azetidine-2(S)-N-(2-aminomethyl-5-chlorobenzyl)carboxamide (Active I) were prepared according to general intravenous formulation procedures.

| Component | Estimated range |
|---|---|
| Active 1 | 0.12–0.50 mg |
| D-glucuronic acid* | 0.5–5 mg |
| Mannitol NF | 50–53 mg |
| 1 N Sodium Hydroxide | q.s. pH 3.9–4.1 |
| Water for injection | q.s. 1.0 mL |

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:
1. A compound of the general formula:

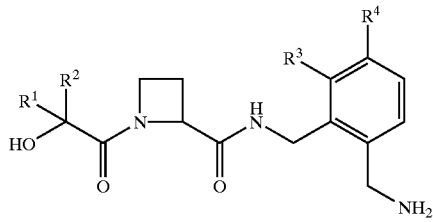

or a pharmaceutically acceptable salt thereof, wherein
$R^1$ and $R^2$ are independently selected from the group consisting of
1) hydrogen,
2) $C_{1-6}$ alkyl,
3) $C_{1-6}$ alkyl substituted with one, two or three members, same or different, selected from the group consisting of
  i) hydroxyl,
  ii) halogen,
  iii) $CF_3$,
  iv) phenyl,
  v) phenyl, substituted with one, two or three members, same or different, selected from the group consisting of
    a) hydroxyl,
    b) halogen,
    c) $CF_3$,
    d) $C_{1-6}$ alkyl,
    e) $C_{1-4}$ alkoxyl,
    f) amino,
    g) $C_{1-4}$ alkylamino, and
    h) $CH_3C(O)NH—$,
  vi) pyridyl,
  vii) pyridyl substituted with one or two members, same or different, selected from the group consisting of
    a) halogen,
    b) $C_{1-4}$ alkoxyl, and
    c) $C_{1-6}$ alkyl,
  viii) pyridyl N-oxide
  ix) pyridyl N-oxide substituted with one or two members, same or different, selected from the group consisting of
    a) halogen,
    b) $C_{1-4}$ alkoxyl, and
    c) $C_{1-6}$ alkyl,
  x) $C_{3-6}$ cycloalkyl, and
  xi) $C_{3-6}$ cycloalkyl substituted with $C_{1-4}$ alkyl or halogen,
4) $C\equiv C—R^8$,
5) phenyl,
6) phenyl substituted with one, two or three members, same or different, selected from the group consisting of
  i) hydroxyl,
  ii) halogen,
  iii) $CF_3$,
  iv) $C_{1-6}$ alkyl,
  v) $C_{1-4}$ alkoxyl,
  vi) amino,
  vii) $C_{1-4}$ alkylamino, and
  viii) $CH_3C(O)NH—$, 7) pyridyl,
8) pyridyl substituted with one or two members, same or different, selected from the group consisting of
   i) halogen,
   ii) $C_{1-4}$ alkoxyl, and
   iii) $C_{1-6}$ alkyl,
9) pyridyl N-oxide,
10) pyridyl N-oxide substituted with one or two members, same or different, selected from the group consisting of
    i) halogen,
    ii) $C_{1-4}$ alkoxyl, and
    iii) $C_{1-6}$ alkyl,
11) $C_{3-6}$ cycloalkyl, and
12) $C_{3-6}$ cycloalkyl substituted with $C_{1-4}$ alkyl or halogen;

$R^3$ is hydrogen or halogen;

$R^4$ is halogen;

$R^8$ is selected from the group consisting of
1) hydrogen,
2) $C_{1-6}$ alkyl,
3) $C_{3-6}$ cycloalkyl, and
4) $C_{3-6}$ cycloalkyl substituted with $C_{1-4}$ alkyl or halogen, provided that when $R^3$ is hydrogen, $R^4$ is Cl, or a pharmaceutically acceptable salt thereof.

2. A compound of claim 1, or a pharmaceutically acceptable salt thereof, wherein $R^3$ is hydrogen or F, and $R^4$ is Cl or F, provided that when $R^3$ is hydrogen, $R^4$ is Cl.

3. A compound of claim 2, or a pharmaceutically acceptable salt thereof, wherein $R^2$ is hydrogen or $C_{1-6}$ alkyl.

4. A compound of claim 3, or a pharmaceutically acceptable salt thereof, wherein $R^1$ is
1) $C_{1-6}$ alkyl, unsubstituted or substituted with one, two, or three members, same or different, selected from the group consisting of
   i) cyclopropyl, and
   ii) cyclopropyl substituted with $C_{1-4}$ alkyl,
2) C≡CC(CH$_3$)$_3$, or
3) phenyl substituted with Cl.

5. A compound of claim 4, or a pharmaceutically acceptable salt thereof, selected from the group consisting of 1-(3,3-Dimethyl-2(R)-hydroxybutanoyl)azetidine-2(S)-N-(2-aminomethyl-5-chlorobenzyl)carboxamide,
1-(4,4-Dimethyl-2(R)-hydroxypentanoyl)azetidine-2(S)-N-(2-aminomethyl-5-chlorobenzyl)carboxamide,
1-(3-(1-Methylcyclopropyl)-2(R)-hydroxypropanoyl)azetidine-2(S)-N-(2-aminomethyl-5-chlorobenzyl)carboxamide,
1-(3(S)-Cyclopropyl-2(R)-hydroxybutanoyl)azetidine-2(S)-N-(2-aminomethyl-5-chlorobenzyl)carboxamide,
1-(3-Cyclopropyl-3-methyl-2(R)-hydroxybutanoyl)azetidine-2(S)-N-(2-aminomethyl-5-chlorobenzyl)carboxamide,
1-(3(R)-Cyclopropyl-2(R)-hydroxybutanoyl)azetidine-2(S)-N-(2-aminomethyl-5-chlorobenzyl)carboxamide,
1-(2-hydroxy-2,5,5-trimethyl-3-hexynoyl)azetidine-2(S)-N-(2-aminomethyl-5-chlorobenzyl)carboxamide,
1-(2(R)-hydroxy(3-chlorophenyl)acetyl)azetidine-2(S)-N-(2-aminomethyl-5-chlorobenzyl)carboxamide,
1-(3-Cyclopropyl-3-methyl-2(R)-hydroxybutanoyl)azetidine-2(S)-N-(2-aminomethyl-6-fluoro-5-chlorobenzyl)carboxamide, and
1-(3,3-Dimethyl-2(R)-hydroxybutanoyl)azetidine-2(S)-N-(2-aminomethyl-5,6-difluorobenzyl)carboxamide.

6. A composition for inhibiting thrombus formation in blood comprising a compound of claim 1 and a pharmaceutically acceptable carrier.

7. A method for inhibiting thrombus formation in a patient comprising administering to the patient a composition of claim 6.

8. A method for inhibiting formation of blood platelet aggregates in a patient comprising administering to the patient a composition of claim 6.

9. A method for treating or preventing venous thromboembolism and pulmonary embolism in a mammal comprising administering to the mammal a composition of claim 6.

10. A method for treating or preventing deep vein thrombosis in a mammal comprising administering to the mammal a composition of claim 6.

11. A method for treating or preventing thromboembolic stroke in humans and other mammals comprising administering to the mammal a composition of claim 6.

* * * * *